Aug. 20, 1957 E. S. BOERNER Plant Pat. 1,635
CHRYSANTHEMUM PLANT
Filed Dec. 5, 1956
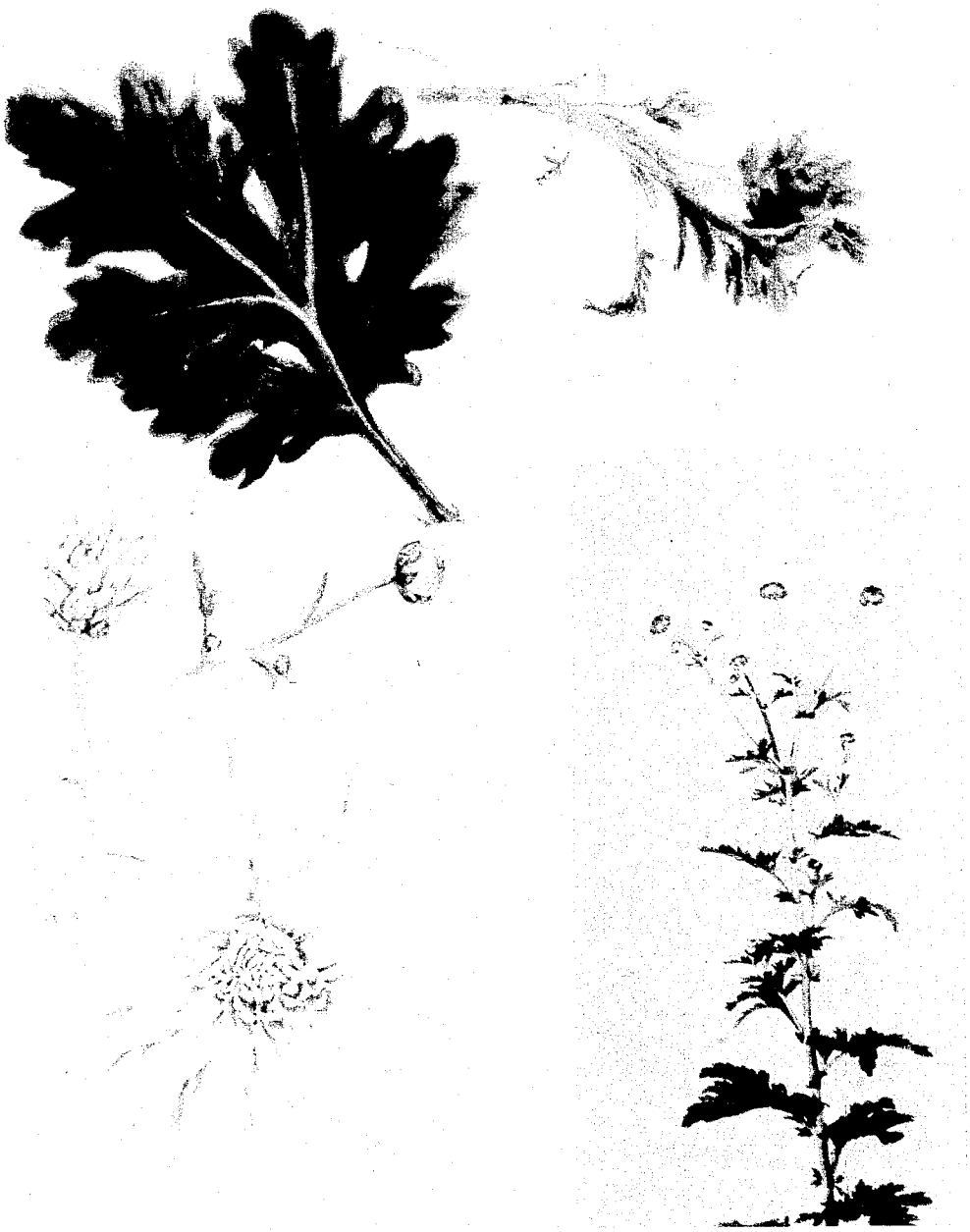
Inventor.
E. S. Boerner
By: Robb & Robb
Attorneys.

United States Patent Office

Plant Pat. 1,635
Patented Aug. 20, 1957

1,635

CHRYSANTHEMUM PLANT

Eugene S. Boerner, Newark, N. Y., assignor to Jackson & Perkins Company, Newark, N. Y., a corporation of New York Application December 5, 1956, Serial No. 626,563

1 Claim. (Cl. 47—60)

The present invention relates to a new and distinct variety of chrysanthemum plant of the decorative type, which was originated by me by crossing the variety "Kingbird" (Plant Patent No. 1,306) with the variety "Tanager" (Plant Patent No. 1,129).

The primary objective of this breeding was to produce a new chrysanthemum variety which bears larger flowers than those customarily borne by Rubellum type chrysanthemums. This objective was fully achieved, as evidenced by the following characteristics which are outstanding in my new variety:

(1) The vigor and hardiness of the plant and flowers;
(2) The large size of the flowers; and
(3) The distinctive Thulite Pink, lightly overcast with Rose Pink, general color tonality of the flowers.

The foregoing characteristics and distinctions definitely differentiate my new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character, and also shows a typical specimen plant in black-and-white which is illustrative of the form and habit of growth of the plant.

The following is a detailed description of my new variety, with color terminology in accordance with Ridgway's Color Standards and Nomenclature, as based upon observations made from specimens grown outdoors at Newark, New York, in the early morning during the latter part of September:

Parentage: "Kingbird" × "Tanager."
Classification: Decorative.
Growth: Upright; vigorous; strong; attains height of from 2½ to 3 feet.

Cold resistance: Plants are very winter-hardy in northern New York, and flowers are frost-resistant.
Blooming period: In the Newark, New York, climatic area, blooming usually begins about September 25th and continues until heavy freezes in October.

*Flower*

Bud:
*Color.*—When sepals first divide—Rhodonite Pink, Plate 38. When petals begin to unfurl—Pale Rhodonite Pink, Plate 38, lightly overcast with Alizarine Pink, Plate 13. When half-blown: Inside—Thulite Pink, Plate 26, lightly overcast with Rose Pink, Plate 12; reverse—Flesh Pink, Plate 13, lightly overcast with Geranium Pink, Plate 1.
*Peduncle.*—Strong. Color—Kildare Green, Plate 31.

Bloom:
*Size.*—From 5½ to 6 inches.
*Stem.*—Long; strong.
*Form.*—Decorative.
*Petalage.*—Very double; wide.
*Color.*—Center of flower—Eosine Pink, Plate 1, lightly overcast with Thulite Pink, Plate 26. Outer petals—Hermosa Pink, Plate 1, lightly overcast with Thulite Pink, Plate 26. Base of petals—Deep Sea-Foam Green, Plate 31. Inside of petals—Thulite Pink, Plate 26, lightly overcast with Rose Pink, Plate 12. Reverse of petals—Cream Color, Plate 16, lightly overcast with Cameo Pink, Plate 26, in the lower half of the petals.
*Petals.*—Texture—medium. Form—Oval pointed.
*Fragrance.*—Characteristic chrysanthemum.

*Plant*

Form: Upright.
Growth: Full; well-branched; with heavy Rubellum characteristics.
Foliage:
*Size.*—Large.
*Quantity.*—Heavy.
*Color.*—Upper side—Varley's Green, Plate 18. Reverse side—Cress Green, Plate 31.
*Texture.*—Leathery.

I claim:

A new and distinct variety of chrysanthemum plant of the decorative type, substantially as herein shown and described, characterized particularly as to novelty by the vigor and hardiness of its plant and flowers, the large size of its flowers, and the Thulite Pink, lightly overcast with Rose Pink, general color tonality of its flowers.

No references cited.